United States Patent [19]

Shaw et al.

[11] Patent Number: 5,696,260

[45] Date of Patent: *Dec. 9, 1997

[54] CERTAIN CYCLOALKYL IMIDAZOPYRIMIDINES, A NEW CLASS OF GABA BRAIN RECEPTOR LIGANDS

[75] Inventors: Kenneth Shaw, Weston; Alan Hutchison, Madison, both of Conn.

[73] Assignee: Neurogen Corporation, Branford, Conn.

[*] Notice: The term of this patent shall not extend beyond the expiration date of Pat. No. 5,185,446.

[21] Appl. No.: 492,806

[22] Filed: Jun. 20, 1995

Related U.S. Application Data

[63] Continuation of Ser. No. 30,122, Mar. 3, 1993, Pat. No. 5,426,186, which is a continuation-in-part of Ser. No. 577,203, Sep. 4, 1990, Pat. No. 5,185,446.

[51] Int. Cl.[6] .................................... C07D 487/04
[52] U.S. Cl. ............................. 544/115; 544/250
[58] Field of Search .............................. 544/250, 115

[56] References Cited

U.S. PATENT DOCUMENTS 5,185,446  2/1993  Shaw et al. ........................ 544/250
5,426,186  6/1995  Shaw et al. ........................ 544/250

*Primary Examiner*—Emily Bernhardt
*Attorney, Agent, or Firm*—McDonnell Boehnen Hulbert & Berghoff

[57] ABSTRACT

Disclosed are compounds of the formula:

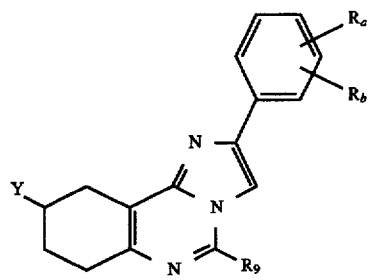

or pharmaceutically acceptable non-toxic salts thereof wherein:

$R_9$ and Y are substituents as defined herein; and $R_a$ and $R_b$ independently represent halogen, hydroxy, amino, mono or dialkylamino where each alkyl is straight or branched chain alkyl having 1–6 carbon atoms, straight or branched chain lower alkyl having 1–6 chain atoms, or straight or branched chain lower alkoxy having 1–6 carbon atoms, where $R_a$ and $R_b$ each appear at most only once on the phenyl ring which compounds are highly selective agonists, antagonists or inverse agonists for GABAa brain receptors or prodrugs thereof and are useful in the diagnosis and treatment of anxiety, sleep, and seizure disorders, overdose with benzodiazepine type drugs, and enhancement of alertness.

1 Claim, 4 Drawing Sheets

Compound 1

Compound 5

Compound 12

Compound 13

Compound 14

Compound 18

Compound 21

Compound 24

Compound 25

Compound 31

Compound 33

Compound 39

Compound 50

Compound 51

CERTAIN CYCLOALKYL IMIDAZOPYRIMIDINES, A NEW CLASS OF GABA BRAIN RECEPTOR LIGANDS

This application is a continuation of U.S. application Ser. No. 08/030,122, filed on Mar. 3, 1993 now U.S. Pat. No. 5,426,186, which is a national phase of International Application No. PCT/US91/06174, filed Sep. 4, 1991, which is a continuation-in-part of U.S. application Ser. No. 07/577,203, filed Sep. 4, 1990 now U.S. Pat. No. 5,185,446.

BACKGROUND OF THE INVENTION

Field of the Invention

This invention relates to certain cycloalkyl imidazopyrimidines which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness. The interaction of 2-aryl substituted imidazopyrimidines of the invention with a GABA binding site, the benzo-diazepines (BDZ) receptor, is described. This interaction results in the pharmacological activities of these compounds.

DESCRIPTION OF THE RELATED ART

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207:274–81. Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepins potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281.).

In 1978, it became clear that GABA and related analogs could interact at the low affinity (1 μM) GABA binding site to enhance the binding of benzodiazepines to the clonazepan-sensitive site (Tallman et al. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274, 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46, Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "Isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into $\alpha$, $\beta$, $\gamma$, $\delta$, $\epsilon$, and provide a molecular basis for the GABAa receptor heterogeneity and distictive regional pharmacology (Shivvers et al., 1980; Levitan et al., 1989). The $\gamma$ subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predicative about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine, (Hunkeler et al., 1981, Nature 290: 514–516). This compound is a high affinity competitive inhibitor of benzodiazepine and beta-carboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and beta-carbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous. A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA [(Braestrup & Nielsen 1981, Nature 294: 472–474)]. Thus, the GABA shift predicts generally the expected behavioral properties of the compounds.

Various compounds have been prepared as benzodiazepine agonists and antagonists. For example, U.S. Pat. Nos. 4,713,383, and 4,643,999 and Eur. Patent Applications Nos. 181,282, 219,748 and 263,071 teach various benzodiazepine agonists and antagonists useful in the treatment of anxiety. U.S. Pat. No. 4,643,999 discloses compounds of the formula:

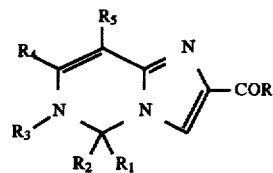

wherein R is an aryl of 6 to 12 carbon atoms, $R_1$ is selected from the group consisting of hydrogen and alkyl, alkoxy and alkylthio of 1 to 5 carbon atoms when $R_2$ and $R_3$ together form a carbon-nitrogen bond or $R_1$ and $R_2$ together are —O when $R_3$ is selected from the group consisting of hydrogen, alkyl of 1 to 5 carbon atoms and alkenyl of 2 to 5 carbon atoms. $R_4$ is selected from the group consisting of alkoxy and alkylthio of 1 to 5 carbon atoms. $R_5$ is selected from the group consisting of hydrogen and alkyl of 1 to 5 carbon atoms, and their non-toxic, pharmaceutically acceptable acid addition salts.

U.S. Pat. No. 4,713,383 teaches compounds of the formula:

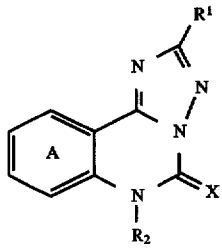

wherein $R_1$=(un)substituted Ph, (dihydro)furanyl, tetrahydrofuranyl, (dihydro)thienyl, tetrahydrothienyl, pyranyl, ribofuranosyl, all C-attached;

$R_2$=H, alkyl; X=O, S, $R_3$N; $R_3$=H, alkenyl, alkynyl, $C_{3-20}$ cycloalkyl, (un)substituted alkyl, aryl, aralkyl, where aryl is Ph, pyridinyl, thienyl, furanyl; ring A may be substituted by alkyl, alkoxy, halo, amino, alkylthio, etc.

European Patent Application EP 181,282 discloses compounds of the formula:

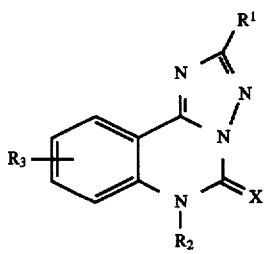

wherein $R_1$=(substituted) Ph or heterocycle;

$R_2$=H, alkyl, alkenyl, hydroxyalkyl, aralkyl, aralkenyl, aryl; $R_3$=H, alkyl, alkoxy, HO, halo, $F_3C$, $O_3N$, $H_2N$, alkylthio, alkylsulfinyl, alkylsulfonyl, aralkoxy; X=O, S, $NR_4$;

$R_4$=H, alkyl, aralkyl, cycloalkyl, alkenyl, alkynyl, aryl, (substituted) aminoalkyl, hydroxyalkyl.

European Patent Application EP 217,748 teaches compounds of the formula:

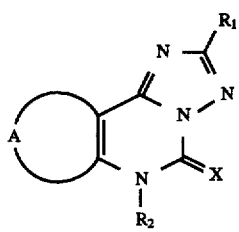

wherein A=atoms to complete a fused, (un)substituted, (un)saturated, carbocyclic or heterocyclic ring comprising C, O, N, and S; X=O, S, RN; R=H, OH, hydroxyalkyl, aryl, $H_2NC(:NH)$, alkyl, alkenyl, alkynyl, optionally with hetero atom interrupters; R=(un)substituted carbocyclyl, heterocyclyl; $R_2$=(un)substituted Ph.

European Patent Application EP 263,071 discloses compounds of the formula

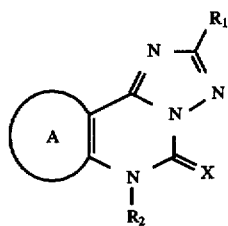

wherein

X=O, NR, S;

R=H, lower alkyl, alkenyl, alkynyl;

$R_1$=(substituted) Ph, furyl, thienyl, pyridyl, pyrrolyl, etc; ring A=$C_{5-8}$ cycloalkene, heterocycle, etc., each ring A being unsubstituted or substituted by lower alkyl, alkoxy, OH, halogen, $CF_3$, $NO_2$, carbamoyl, carbamoylalkyl, etc.

These compounds differ from the compounds of the present invention. U.S. Pat. No. 4,713,383, and European Patent Applications Nos. 181,282, 217,748 and 263,071. Each teach carbocyclic compounds having an additional nitrogen atom in the carbocyclic system. U.S. Pat. No. 4,643,999 teaches imidazopyrimidines lacking the aryl substituents at position 2, the nitrogen in the ring system at position 9, and other various ring substituents of the compounds of the present invention.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in enhancing alertness, treatment of seizure, anxiety, and sleep disorders, and treatment of benzodiazepine overdoses. Accordingly, a broad embodiment of the invention is directed to compounds of Formula I:

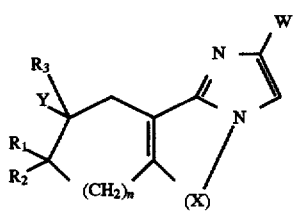

and pharmaceutically acceptable non-toxic salts thereof wherein:

n is 0, 1 or 2;

$R_1$, $R_2$, and $R_3$ are the same or different and represent hydrogen or straight chain or branched lower alkyl having 1–6 carbon atoms;

W is phenyl, thienyl, oxazolyl, 1,3,4-oxadiazolyl or pyridyl; or phenyl, thienyl, oxazolyl, 1,3,4-oxadiazolyl or pyridyl, each of which is mono or disubstituted with halogen, hydroxy, amino, mono or dialkylamino, straight or branched chain lower alkyl having 1–6 carbon atoms, or straight or branched chain lower alkoxy having 1–6 carbon atoms;

Y is

—$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms;

—$CONR_4R_5$ or —$(CH_2)_nNR_4R_5$ where n=0, 1, or 2, $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;

—$CONR_4R_5$ or —$(CH_2)_nNR_4R_5$ where n=0, 1 or 2, and $NR_4R_5$ is N-alkyl-piperazyl, -morpholyl, -piperidyl, or -pyrrolidyl where each alkyl portion is straight or branched chain lower alkyl having 1–6 carbon atoms;

$NR_4CO_2R_6$ where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or —$C(OH)R_7R_8$ where $R_7$ and $R_8$ are the same or different and represent straight or branched chain lower alkyl having 1 to 6 carbon atoms, phenyl or phenylalkyl where each alkyl portion is straight or branched chain lower alkyl having 1–6 carbon atoms;

X is $$-N=C-R_9 \text{ or } -NR_{10}-C=T,$$

with the proviso that when X is $$-NR_{10}C=T.$$

T is oxygen or sulfur and $R_{10}$ is
hydrogen, straight or branched chain lower alkyl containing 1–6 carbon atoms; or
$COR_{11}$ where $R_{11}$ is hydrogen, amino, straight or branched chain lower alkyl having 1–6 carbon atoms, alkoxy having 1–6 carbon atoms, or dialkylamino where each alkyl portion is straight or branched chain lower alkyl having 1–6 carbon atoms; and
when X is $$-N=C-R_9.$$

$R_9$ is
hydrogen, halogen, cyano, aryloxy, or alkoxy having 1–6 carbon atoms, amino, phenylamino, mono- or dialkylamino where each alkyl portion is straight or branched chain alkyl having 1–6 carbon atoms, phenylalkyl amino where the alkyl portion is a straight or branched chain lower alkyl having 1–6 carbon atoms;
$COR_{11}$ where $R_{11}$ is hydrogen, amino, straight or branched chain lower alkyl having 1–6 carbon atoms, alkoxy having 1–6 carbon atoms, or dialkylamino where each alkyl portion is straight or branched chain lower alkyl having 1–6 carbon atoms; or
$CONHR_{12}$ where $R_{12}$ is hydrogen or straight or branched chain lower alkyl having 1 to 6 carbon atoms.

These compounds are highly selective agonists, antagonists or inverse agonists for GABAa brain receptors or prodrugs thereof and are useful in the diagnosis and treatment of anxiety, sleep, and seizure disorders, overdose with benzodiazepine drugs, and enhancement of memory.

DETAILED DESCRIPTION OF THE INVENTION

Figure 1A:
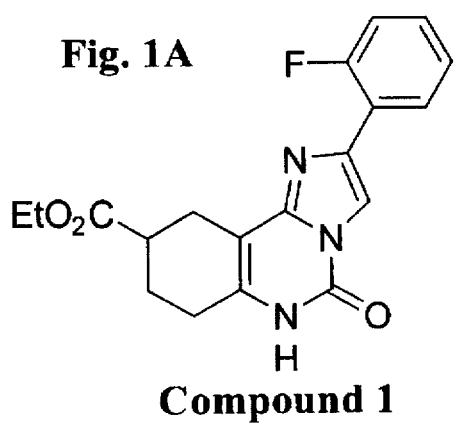
FIGS. 1A–N show representative 2-aryl substituted imidazo[1,2-c]quinazolines of the present invention.

The novel compounds encompassed by the instant invention can be described by general formula I:

and pharmaceutically acceptable non-toxic salts thereof wherein:

n is 0, 1 or 2;

$R_1$, $R_2$, and $R_3$ are the same or different and represent hydrogen or straight chain or branched lower alkyl having 1–6 carbon atoms;

W is
phenyl, thienyl, oxazolyl, 1,3,4-oxadiazolyl or pyridyl; or
phenyl, thienyl, oxazolyl, 1,3,4-oxadiazolyl or pyridyl, each of which is mono or disubstituted with halogen, hydroxy, amino, mono or dialkylamino, straight or branched chain lower alkyl having 1–6 carbon atoms, or straight or branched chain lower alkoxy having 1–6 carbon atoms;

Y is
—$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms;

—$CONR_4R_5$ or —$(CH_2)_nNR_4R_5$ where n=0, 1, or 2. $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;

—$CONR_4R_5$ or —$(CH_2)_nNR_4R_5$ where n=0, 1, or 2, and $NR_4R_5$ is N-alkyl-piperazyl, -morpholyl, -piperidyl, or -pyrrolidyl where each alkyl portion is straight or branched chain lower alkyl having 1–6 carbon atoms;

$NR_4CO_2R_6$ where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or —$C(OH)R_7R_8$ where $R_7$ and $R_8$ are the same or different and represent straight or branched chain lower alkyl having 1 to 6 carbon atoms, phenyl or phenylalkyl where each alkyl portion is straight or branched chain lower alkyl having 1–6 carbon atoms;

X is $$-N=\overset{|}{C}-R_9 \quad \text{or} \quad -NR_{10}-\overset{|}{C}=T,$$

with the proviso that when X is $$-NR_{10}\overset{|}{C}=T,$$

T is oxygen or sulfur and $R_{10}$ is
- hydrogen, straight or branched chain lower alkyl containing 1–6 carbon atoms; or
- $COR_{11}$ where $R_{11}$ is hydrogen, amino, straight or branched chain lower alkyl having 1–6 carbon atoms, alkoxy having 1–6 carbon atoms, or dialkylamino where each alkyl portion is straight or branched chain lower alkyl having 1–6 carbon atoms; and when X is $$-N=\overset{|}{C}-R_9,$$

$R_9$ is
- hydrogen, halogen, cyano, aryloxy, or alkoxy having 1–6 carbon atoms, amino, phenylamino, mono- or dialkylamino where each alkyl portion is straight or branched chain alkyl having 1–6 carbon atoms, phenylalkyl amino where the alkyl portion is a straight or branched chain lower alkyl having 1–6 carbon atoms;
- $COR_{11}$ where $R_{11}$ is hydrogen, amino, straight or branched chain lower alkyl having 1–6 carbon atoms, alkoxy having 1–6 carbon atoms, or dialkylamino where each alkyl portion is straight or branched chain lower alkyl having 1–6 carbon atoms; or
- $CONHR_{12}$ where $R_{12}$ is hydrogen or straight or branched chain lower alkyl having 1 to 6 carbon atoms.

The invention also encompasses compounds of formula II:

and pharmaceutically acceptable non-toxic salts thereof wherein:

W is
- phenyl, thienyl, oxazolyl, 1,3,4-oxadiazolyl or pyridyl; or
- phenyl, thienyl, oxazolyl, 1,3,4-oxadiazolyl or pyridyl, each of which is mono or disubstituted with halogen, hydroxy, amino, mono or dialkylamino, straight or branched chain lower alkyl having 1–6 carbon atoms, or straight or branched chain lower alkoxy having 1–6 carbon atoms;

Y is
- —$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms;
- —$CONR_4R_5$ or —$(CH_2)_nNR_4R_5$ where n=0, 1, or 2, $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;
- —$CONR_4R_5$ or —$(CH_2)_nNR_4R_5$ where n=0, 1, or 2, and $NR_4R_5$ is N-alkyl-piperazyl, -morpholyl, -piperidyl, or -pyrrolidyl where each alkyl portion is straight or branched chain lower alkyl having 1–6 carbon atoms;
- $NR_4CO_2R_6$ where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or
- —$C(OH)R_7R_8$ where $R_7$ and $R_8$ are the same or different and represent straight or branched chain lower alkyl having 1 to 6 carbon atoms, phenyl, or phenylalkyl where each alkyl portion is straight or branched chain lower alkyl having 1–6 carbon atoms; and $R_9$ is
- hydrogen, halogen, aryloxy, alkoxy having 1–6 carbon atoms or $OCOR_{11}$ where $R_{11}$ is hydrogen, amino, straight or branched chain alkyl having 1–6 carbon atoms, alkoxy having 1–6 carbon atoms, or dialkyl amino where each alkyl is a straight or branched chain alkyl having 1–6 carbon atoms.

The invention additionally encompasses compounds of formula III:

and pharmaceutically acceptable non-toxic salts thereof wherein:

W is
- phenyl, thienyl, oxazolyl, 1,3,4-oxadiazolyl or pyridyl; or
- phenyl, thienyl, oxazolyl, 1,3,4-oxadiazolyl or pyridyl, each of which is mono or disubstituted with halogen, hydroxy, amino, mono or dialkylamino, straight or branched chain lower alkyl having 1–6 carbon atoms, or straight or branched chain lower alkoxy having 1–6 carbon atoms;

Y is

—$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms;

—$CONR_4R_5$ or —$(CH_2)_nNR_4R_5$ where n=0, 1, or 2, $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;

—$CONR_4R_5$ or —$(CH_2)_nNR_4R_5$ where n=0, 1, or 2, and $NR_4R_5$ is N-alkyl-piperazyl, -morpholyl, -piperidyl, or -pyrrolidyl where each alkyl portion is straight or branched chain lower alkyl having 1–6 carbon atoms;

$NR_4CO_2R_6$ where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or —$C(OH)R_7R_8$ where $R_7$ and $R_8$ are the same or different and represent straight or branched chain lower alkyl having 1 to 6 carbon atoms, phenyl or phenylalkyl where each alkyl portion is straight or branched chain lower alkyl having 1–6 carbon atoms; and T is oxygen or sulfur.

Furthermore the invention encompasses compounds of formula IV:

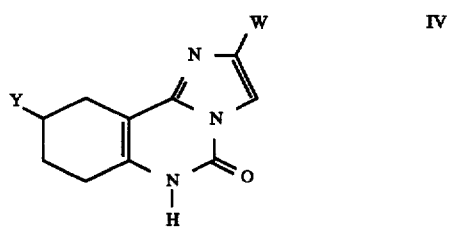

and pharmaceutically acceptable non-toxic salts thereof wherein:

W is phenyl, thienyl, oxazolyl, 1,3,4-oxadiazolyl or pyridyl; or phenyl, thienyl, oxazolyl, 1,3,4-oxadiazolyl or pyridyl, each of which is mono or disubstituted with halogen, hydroxy, amino, mono or dialkylamino, straight or branched chain lower alkyl having 1–6 carbon atoms, or straight or branched chain lower alkoxy having 1–6 carbon atoms;

Y is

—$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms;

—$CONR_4R_5$ or —$(CH_2)_nNR_4R_5$ where n=0, 1, or 2, $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;

—$CONR_4R_5$ or —$(CH_2)_nNR_4R_5$ where n=0, 1, or 2, and $NR_4R_5$ is N-alkyl-piperazyl, -morpholyl, -piperidyl, or -pyrrolidyl where each alkyl portion is straight or branched chain lower alkyl having 1–6 carbon atoms;

$NR_4CO_2R_6$ where $R_4$ is hydrogen, phenyl, thienyl, straight or branched chain lower alkyl having 1–6 carbon atoms, phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or —$C(OH)R_7R_8$ where $R_7$ and $R_8$ are the same or different and represent straight or branched chain lower alkyl having 1 to 6 carbon atoms, phenyl or phenylalkyl where each alkyl portion is straight or branched chain lower alkyl having 1–6 carbon atoms.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Figure 1B:
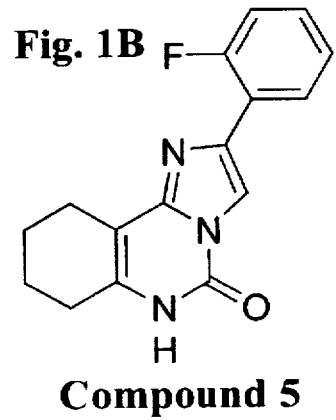
Figure 1C:
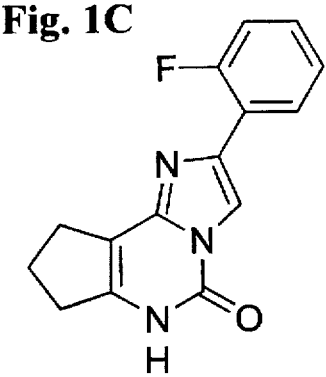
Figure 1D:
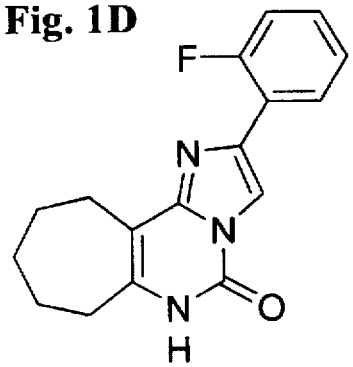
Figure 1E:
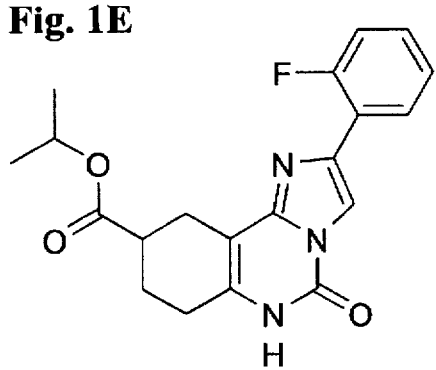
Figure 1F:
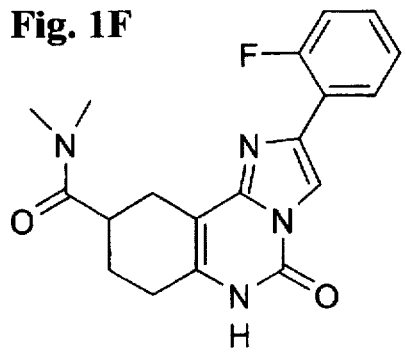
Figure 1G:
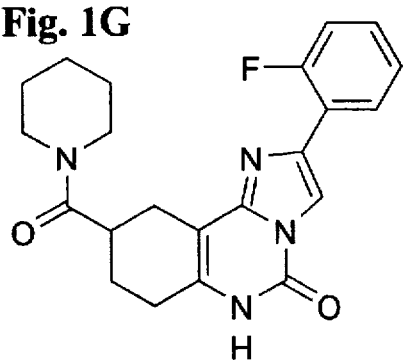
Figure 1H:
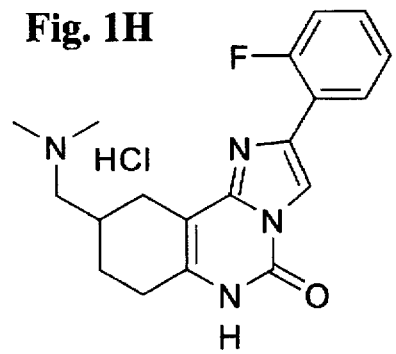
Figure 1I:
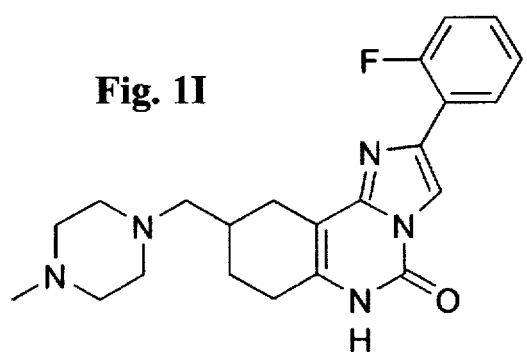
Figure 1J:
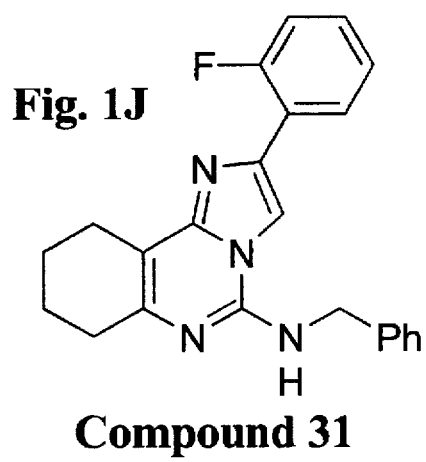
Figure 1K:
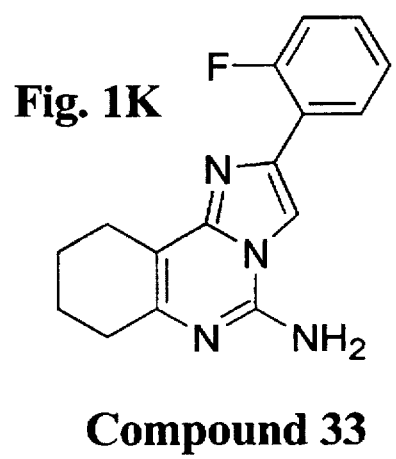
Figure 1L:
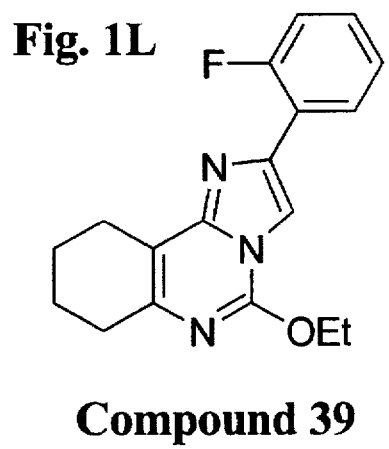
Figure 1M:
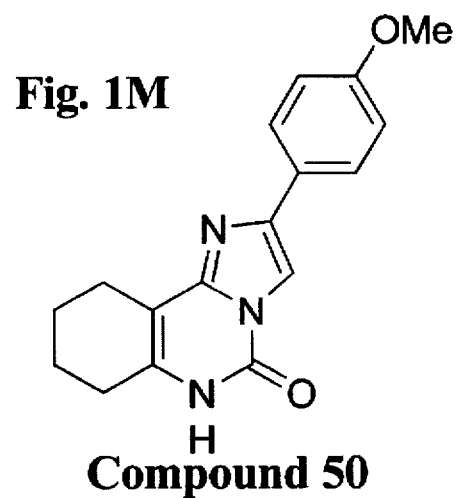
Figure 1N:
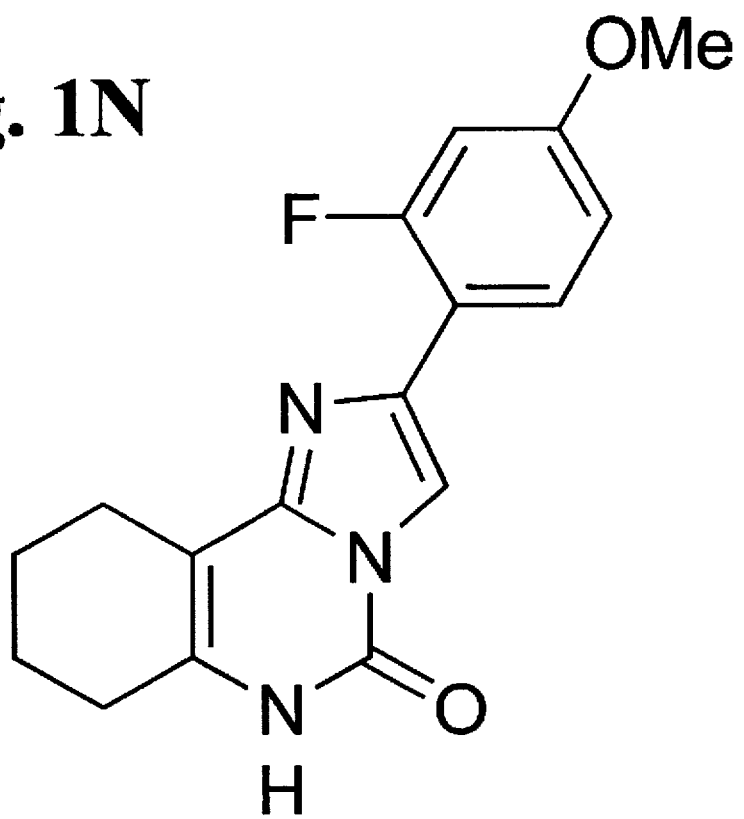

Representative compounds of the present invention, which are encompassed by Formula I, include, but are not limited to the compounds in FIG. 1 and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By lower alkoxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

By N-alkylpiperazyl in the invention is meant radicals of the formula:

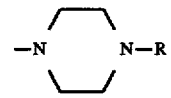

where R is a straight or branched chain lower alkyl as defined above.

The pharmaceutical utility of compounds of this invention are indicated by the following assay for GABAa receptor activity.

Assays are carried out as described in Thomas and Tallman (J. Bio. Chem. 156: 9838–9842, J. Neurosci. 3:433–440, 1983). Rat cortical tissue is dissected and homogenized in 25 volumes (w/v) of 0.05M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05M Tris HCl buffer (pH 7.4 at 40° C.).

Incubations contain 100 µl of tissue homogenate, 100 µl of radioligand 0.5 nM ($^3$H-RO15-1788 specific activity 80 Ci/mmol), drug or blocker and buffer to a total volume of 500 µl. Incubations are carried for 30 min at 4° C. then are rapidly filtered through GFB filters to separate free and bound ligand. Filters are washed twice with fresh 0.05M Tris HCl buffer (pH 7.4 at 4° C.) and counted in a liquid scintillation counter. 1.0 µM diazepam is added to some tubes to determine nonspecific binding. Data are collected in triplicate determinations, averaged and % inhibition of total specific binding is calculated. Total Specific Binding=Total−Nonspecific. In some cases, the amounts of unlabeled drugs is varied and total displacement curves of binding are carried out. Data are converted to a form for the calculation of $IC_{50}$ and Hill Coefficient ($n_H$). Data for the compounds of this invention are listed in Table I.

TABLE I

| Compound Number[1] | $IC_{50}$ (µM) |
|---|---|
| 1 | 0.007 |
| 5 | 0.007 |
| 12 | 0.400 |
| 13 | 0.800 |
| 14 | 0.010 |
| 18 | 0.010 |
| 21 | 0.003 |
| 24 | 0.030 |
| 25 | 0.003 |
| 28 | 0.150 |
| 31 | 2.0 |
| 33 | 0.100 |
| 39 | 5.0 |
| 50 | 0.05 |
| 51 | 0.003 |

[1]Compound numbers relate to compounds shown in FIG I.

Compounds 1, 5, 21, 25, 50 and 51 are particularly preferred embodiments of the present invention because of their potency in binding to the GABAa receptor.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oil phase may be a vegetable oil, for example olive oil or arachis oil, or a mineral oil, for example liquid paraffin or mixture of these. Suitable emulsifying agents may be naturally-occurring phosphatides, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Schemes I and II.

Scheme I

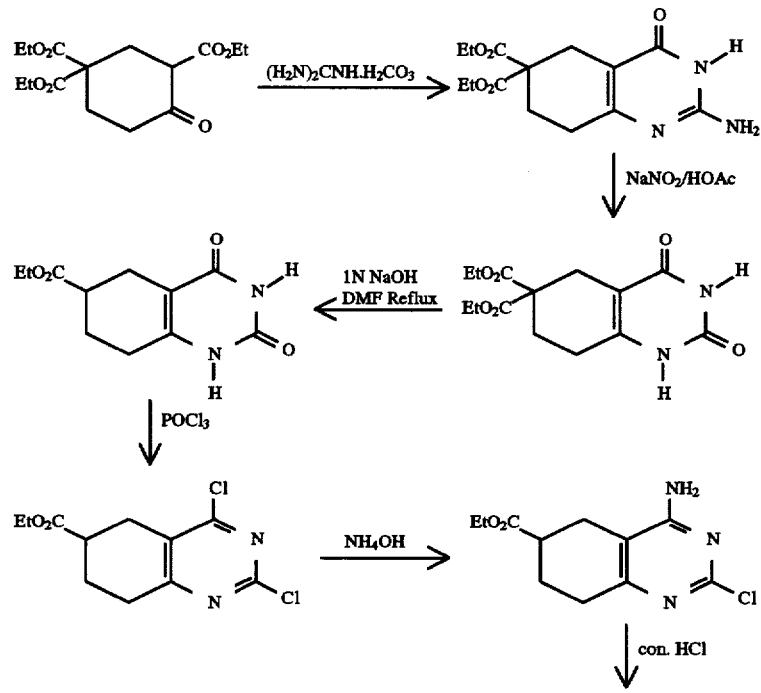

-continued
Scheme I

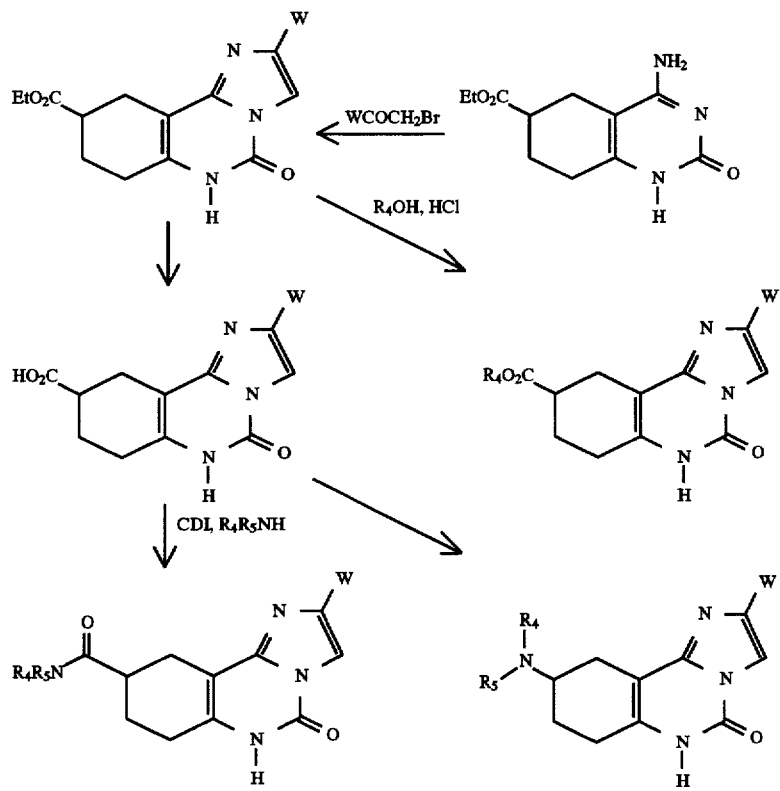

Scheme II

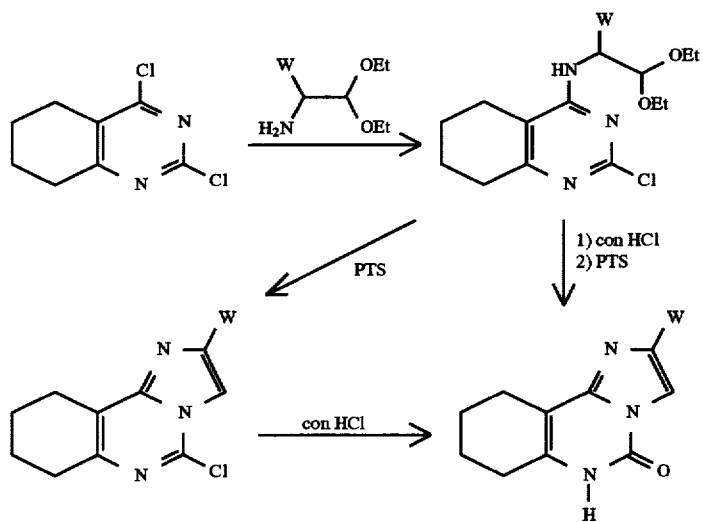

wherein $R_4$, $R_5$, and W are as defined above.

Those having skill in the art will recognize that the starting materials may be varied and additional steps employed to produce compounds encompassed by the present invention, as demonstrated by the following examples.

The invention is illustrated further by the following examples which are not to be construed as limiting the invention in scope or spirit to the specific procedures and compounds described in them.

EXAMPLE I

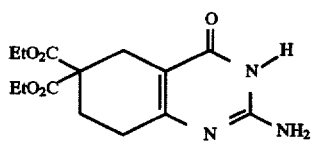

A mixture of Ethyl-4,4-dicarboethoxycyclohexanone-2-carboxylate (100 g) and gunidine carbonate (18.9 g) and dry ethanol (200 mL) was refluxed for 2.5 h. The mixture was cooled and 300 mL water and 20 mL acetic acid were added. The precipitate that formed was collected and air dried to yield 2-Amino-6,6-dicarboethoxy-5,6,7,8-tetrahydro-4(3H)-quinazolinone.

EXAMPLE II

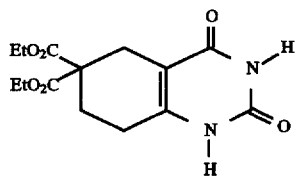

To a solution of 2-Amino-6,6-dicarboethoxy-5,6,7,8-tetrahydro-4(3H)-quinazolinone (75 g) in acetic acid (250 mL) at reflux was added a solution of sodium nitrite (75 g) in water (100 mL) in a dropwise fashion over a period of 45 min. The solution was cooled and the solvent removed in vacuo. The subsequent addition of 300 mL of water precipitated a solid which was collected and dried to yield 6,6-Dicarboethoxy-5,6,7,8-tetrahydro-2,4(1H,3H)-quinazolinedione.

EXAMPLE III

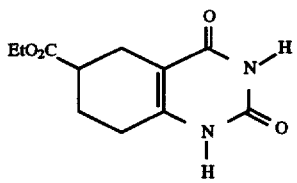

A solution of of 6,6-Dicarboethoxy-5,6,7,8-tetrahydro-2,4(1H,3H)-quinazolinedione (25 g) in 1N NaOH (350 mL) was stirred at 40° C. for 35 min. The solution was cooled in an ice bath and acidified with 35 mL of concentrated HCl. The precipitate that formed was collected and refluxed in 20 ml of dimethylformamide (DMF) for 2 h. The reaction was cooled and the DMF removed in vacuo. To the resulting mixture 40 mL of water was added and the solid collected and dried to yield 6-Carboethoxy-5,6,7,8-tetrahydro-2,4(1H,3H)-quinazolinedione.

EXAMPLE IV

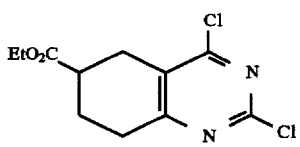

A mixture of 6-Carboethoxy-5,6,7,8-tetrahydro-2,4(1H,3H)-quinazolinedione (7.12 g) and $POCl_3$ (100 mL) was refluxed overnight. The mixture was cooled and the excess $POCl_3$ removed in vacuo. After the mixture was further cooled to 0° C., 20 mL of dry ethanol was added and the resulting mixture neutralized to pH 7 with 10% aqueous ammonium hydroxide. The solid which precipitated was collected and dried to yield 6-Carboethoxy-2,4-dichloro-5,6,7,8-tetrahydroquinazoline.

EXAMPLE V

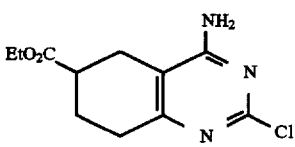

A mixture of 6-Carboethoxy-2,4-dichloro-5,6,7,8-tetrahydroquinazoline (7.68 g), 2-propanol (7 mL) and 30% ammonium hydroxide (12 mL) was heated in a sealed tube at 130° C. for 20 min. The tube was cooled and 20 mL of $H_2O$ was added to the mixture. The solid which precipitated was collected and dried to yield 4-Amino-6-carboethoxy-2-chloro-5,6,7,8-tetrahydroquinazoline.

EXAMPLE VI

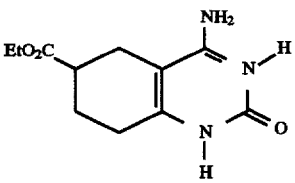

A mixture of 4-Amino-6-carboethoxy-2-chloro-5,6,7,8-tetrahydroquinazoline (6.4 g) and concentrated HCl (10 mL) was refluxed for 20 min. After the solvent was removed in vacuo, 250 ml ethanol saturated with HCl was added, and the mixture was further refluxed for 1 hour. The solvent was subsequently removed in vacuo and 15 ml of water was added to the mixture. The solution was then brought to pH 4 with 30% ammonium hydroxide and the solid subsequently collected and dried to yield 4-Amino-6-carboethoxy-5,6,7,8-tetrahydro-2(1H)-quinazolinone.

EXAMPLE VII

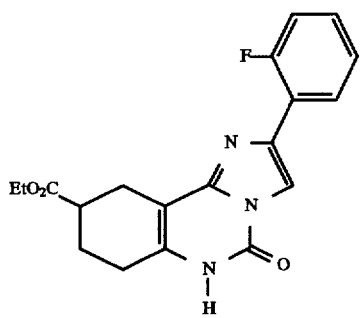

Compound 1

A solution of 4-Amino-6-carboethoxy-5,6,7,8-tetrahydro-2(1H)-quinazolinone (262 mg) and 2'-fluorobromoacetophenone (217 mg) in dry DMF (10 mL) was refluxed under nitrogen for 1.5 h. The solution was cooled and 40 mL water is added. The precipitate was collected and washed successively with 10 mL of methanol and 20 mL hot ethyl acetate to yield 9-Carboethoxy-2-(2-fluorophenyl)-7,8,9,10-tetrahydro-imidazo[1,2-c]-quinazolin-5(6H)-one (Compound 1), m.p. 257°–277° C.

EXAMPLE VIII

The following compounds were prepared essentially according to the procedures described in Examples I–VII:

(a) 2-(4-Chlorophenyl)-7,8,9,10-tetrahydro-imidazo[1,2-c]-quinazolin-5(6H)-one (Compound 2), m.p. 305°–307° C.
(b) 2-(2-Methoxyphenyl)-7,8,9,10-tetrahydro-imidazo[1,2-c]-quinazolin-5(6H)-one (Compound 3), m.p. 283°–285° C.
(c) 2-(2-Chlorophenyl)-7,8,9,10-tetrahydro-imidazo[1,2-c]-quinazolin-5(6H)-one (Compound 4), m.p. 281°–283° C.
(d) 2-(2-Fluorophenyl)-7,8,9,10-tetrahydro-imidazo[1,2-c]-quinazolin-5(6H)-one (Compound 5), m.p. 314°–315° C.
(e) 2-(4-Fluorophenyl)-7,8,9,10-tetrahydro-imidazo[1,2-c]-quinazolin-5(6H)-one (Compound 6), m.p. 301°–303° C.
(f) 2-(3-Chlorophenyl)-7,8,9,10-tetrahydro-imidazo[1,2-c]-quinazolin-5(6H)-one (Compound 7), m.p. 302°–303° C.
(g) 2-Phenyl-7,8,9,10-tetrahydro-imidazo[1,2-c]-quinazolin-5(6H)-one (Compound 8), m.p. 314°–315° C.
(h) 2-(3-Fluorophenyl)-7,8,9,10-tetrahydro-imidazo[1,2-c]-quinazolin-5(6H)-one (Compound 9), m.p. 295°–296° C.
(i) 9-Carboethoxy-2-(3-fluorophenyl)-7,8,9,10-tetrahydro-imidazo[1,2-c]-quinazolin-5(6H)-one (Compound 10), m.p. 227°–228° C.
(j) 2-(4-Methoxyphenyl)-7,8,9,10-tetrahydro-imidazo[1,2-c]-quinazolin-5(6H)-one (Compound 11).
(k) 2-Phenyl-8,9-dihydro-7H-cyclopent[g]-imidazo[1,2-c]-pyrimidin-5(6H)-one (Compound 12), m.p. 281°–282° C.
(l) 2-Phenyl-8,9,10,11-7H-cyclohept[g]-imidazo[1,2-c]-pyrimidin-5(6H)-one (Compound 13), m.p. 283°–285° C.

EXAMPLE IX

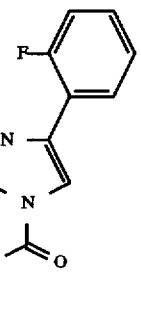

Compound 14

To 10 mL of 2-propanol saturated with HCl gas was added 9-Carboethoxy-2-(2-fluorophenyl)-7,8,9,10-tetrahydro-imidazo[1,2-c]-quinazolin-5(6H)-one (100 mg) and the mixture was heated in a sealed tube at 150° C. for 1 h. The reaction was cooled and the solvent was evaporated in vacuo. To the reaction mixture was added 10 mL of $H_2O$ and the mixture was then brought to pH 7 with ammonium hydroxide. The solid was collected and dried to yield 9-Carboisopropoxy-2-(2-fluorophenyl)-7,8,9,10-tetrahydroimidazo[1,2-c]-quinazolin-5(6H)-one (Compound 14), m.p. 282°–285° C.

EXAMPLE X

The following compounds were prepared essentially according to the procedure of Example IX:

(a) 9-Carboisopropoxy-2-(3-fluorophenyl)-7,8,9,10-tetrahydroimidazo[1,2-c]-quinazolin-5(6H)-one (Compound 15), m.p. 270°–272° C.
(b) 9-Carbobutoxy-2-(2-fluorophenyl)-7,8,9,10-tetrahydroimidazo[1,2-c]-quinazolin-5(6H)-one (Compound 16), m.p. 218°–220° C.

EXAMPLE XI

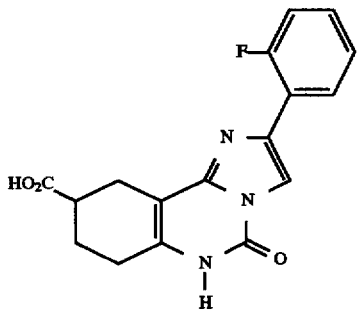

Compound 17

To 20 mL of 1N NaOH was added 9-Carboethoxy-2-(2-fluorophenyl)-7,8,9,10-tetrahydro-imidazo[1,2-c]-quinazolin-5(6H)-one (400 mg). After the solid dissolved, the mixture was stirred for 40 minutes at 60° C., cooled and the pH adjusted to 3 with concentrated HCl. The solid was collected and dried to yield 9-Carboxy-2-(2-fluorophenyl)-7,8,9,10-tetrahydro-imidazo[1,2-c]-quinazolin-5(6H)-one (Compound 17), m.p.>325° C.

EXAMPLE XII

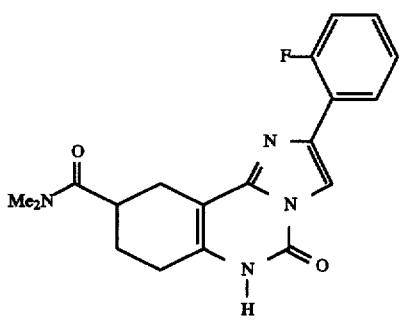

Compound 18

A mixture containing 9-Carboxy-2-(2-fluorophenyl)-7,8,9,10-tetrahydro-imidazo[1,2-c]-quinazolin-5(6H)-one (150 mg) and 1,1-carbonyldiimadazole (120 mg) in DMF (5 mL) was heated to 60° C. for 15 min after which time the reaction was cooled and 2 mL of dimethylamine added. The reaction was allowed to stand at room temperature for 1 hour. To the mixture was then added 10 mL of H$_2$O and the resultant product was collected and dried to yield 9-(N,N-Dimethylcarbamyl)-2-(2-fluorophenyl)-7,8,9,10-tetrahydro-imidazo[1,2-c]-quinazolin-5(6H)-one (Compound 18), m.p.>325° C.

EXAMPLE XIII

The following compounds were prepared essentially according to the procedure of Example XII:
(a) 9-(N-Methylpiperazinecarbonyl)-2-(2-fluorophenyl)-7,8,9,10-tetrahydro-imidazo[1,2-c]-quinazolin-5(6H)-one (Compound 19), m.p.312°-314° C.
(b) 9-(N-Benzylcarbamyl)-2-(2-fluorophenyl)-7,8,9,10-tetrahydroimidazo[1,2-c]-quinazolin-5(6H)-one (Compound 20), m.p.305°-306° C.
(c) 9-(Piperidinecarbonyl)-2-(2-fluorophenyl)-7,8,9,10-tetrahydroimidazo[1,2-c]-quinazolin-5(6H)-one (Compound 21).
(d) 9-(Pyrrolidinecarbonyl)-2-(2-fluorophenyl)-7,8,9,10-tetrahydroimidazo[1,2-c]-quinazolin-5(6H)-one (Compound 22).
(e) 9-(Morpholinecarbonyl)-2-(2-fluorophenyl)-7,8,9,10-tetrahydroimidazo[1,2-c]-quinazolin-5(6H)-one (Compound 23).

EXAMPLE XIV

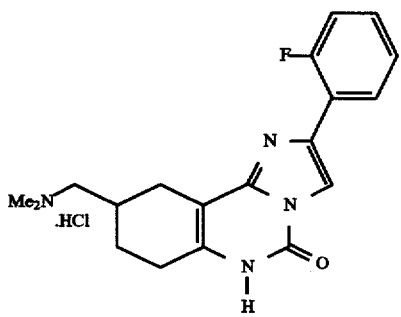

Compound 24

To 100 mL of anhydrous tetrahydrofuron was added 9-(N,N-Dimethylcarbamyl)-2-(2-fluorophenyl)-7,8,9,10-tetrahydro-imidazo[1,2-c]-quinazolin-5(6H)-one (70 mg). The mixture was refluxed until the solid had completely dissolved. Refluxing was ceased and 100 mg of lithium aluminum hydride was added to the solution. This mixture was allowed to stand for 20 min before being quenched with ethyl acetate. The quenched reaction mixture was filtered through celite and the solvent removed in vacuo to yield an oil. The oil was then dissolved in 5 mL of ethyl acetate and to this ethyl acetate solution was added 1 mL of HCl saturated ethyl acetate. A solid precipitated was collected and dried to yield 9-(N,N-Dimethylaminomethyl)-2-(2-fluorophenyl)-7,8,9,10-tetrahydro-imidazo[1,2-c]-quinazolin-5(6H)-one monohydrochloride (Compound 24), m.p.>325° C.

EXAMPLE XV

The following compound was prepared essentially according to the procedure of Example XIV:
(a) 9-(N-Methylpiperazinylmethyl)-2-(2-fluorophenyl)-7,8,9,10-tetrahydro-imidazo[1,2-c]-quinazolin-5(6H)-one monohydrochloride (Compound 25). m.p.325°-327° C.
(b) 9-(Piperidinylmethyl)-2-(2-fluorophenyl)-7,8,9,10-tetrahydro-imidazo[1,2-c]-quinazolin-5(6H)-one monohydrochloride (Compound 26). m.p.223°-226° C.
(c) 9-(Hydroxymethyl)-2-(2-fluorophenyl)-7,8,9,10-tetrahydro-imidazo[1,2-c]-quinazolin-5(6H)-one (Compound 27). m.p.273°-274° C.

EXAMPLE XVI

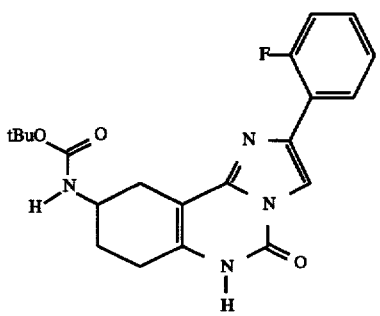

Compound 28

To 10 mL of anhydrous t-butanol was added 9-Carboxy-2-(2-fluorophenyl)-7,8,9,10-tetrahydro-imidazo[1,2-c]-quinazolin-5(6H)-one (327 mg), diphenylphosphorylazide 275 mg), and triethylamine (100 mg). The resulting mixture was refluxed for 14 hours and the solvent removed in vacuo. The mixture was then triterated with 10 mL hot methanol and the resultant solid was collected, washed with ethyl acetate, and dried to yield 9-(t-Butoxycarbonylamino)-2-(2-fluorophenyl)-7,8,9,10-tetrahydro-imidazo[1,2-c]-quinazolin-5(6H)-one (Compound 28), m.p.>325° C.

EXAMPLE XVII

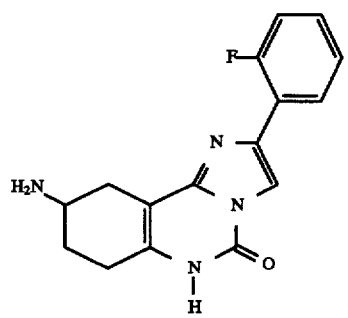

Compound 29

To 10 mL of trifluoroacetic acid was added 9-(t-Butoxycarbonylamino)-2-(2-fluorophenyl)-7,8,9,10-tetrahydro-imidazo[1,2-c]-quinazolin-5(6H)-one (100 mg).

After the solid dissolved, the solution was stirred for 20 minutes and the TFA removed in vacuo. To the residue was added 10 mL of water followed by sufficient saturated aqueous sodium bicarbonate to neutralize the mixture. The mixture was subsequently cooled and the solid collected to yield 9-Amino-2-(2-fluorophenyl)-7,8,9,10-tetrahydroimidazo[1,2-c]-quinazolin-5(6H)-one (Compound 29), m.p.>325° C.

EXAMPLE XVIII

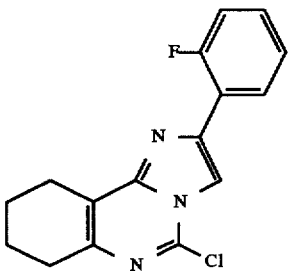

Compound 30

To 50 mL of POCl₃ was added 2-(2-Fluorophenyl)-7,8,9,10-tetrahydro-imidazo[1,2-c]-quinazolin-5(6H)-one (600 mg) and the resultant mixture was refluxed for 48 h. The mixture was then cooled and the POCl₃ was removed in vacuo. To the residue was added 20 mL of water and the pH adjusted to 7 with ammonium hydroxide. After cooling, the precipitated solid was collected to yield 5-Chloro-2-(2-fluorophenyl)-7,8,9,10-tetrahydro-imidazo[1,2-c]-quinazoline (Compound 30), m.p. 175°–176° C.

EXAMPLE XIX

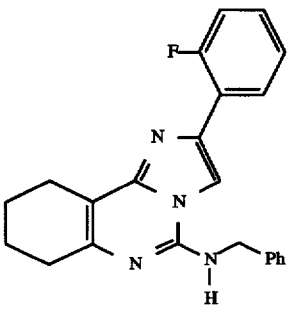

Compound 31

To 5 mL of benzylamine was added 5-Chloro-2-(2-fluorophenyl)-7,8,9,10-tetrahydro-imidazo[1,2-c]-quinazoline (150 mg) and the resulting mixture heated at 100° C. for 20 min. After 10 mL of water was added to the mixture, it was cooled and the solid that precipitated was collected. The solid was recrystallized from ethanol/water to yield 5-(N-benzylamino)-2-(2-fluorophenyl)-7,8,9,10-tetrahydro-imidazo[1,2-c]-quinazoline (Compound 31), m.p. 144°–145° C.

EXAMPLE XX

The following compounds were prepared according to the procedure of Examples XVIII and XIX:
(a) 5-Chloro-2-phenyl-7,8,9,10-tetrahydro-imidazo[1,2-c]-quinazoline (Compound 32), m.p. 145°–146° C.
(b) 5-Amino-2-(2-fluorophenyl)-7,8,9,10-tetrahydro-imidazo[1,2-c]-quinazoline (Compound 33), m.p. 255°–258° C.
(c) 5-(N,N-Dimethylamino)-2-(2-fluorophenyl)-7,8,9,10-tetrahydro-imidazo[1,2-c]-quinazoline (Compound 34), m.p. 158°–160° C.
(d) 5-(N-Propylamino)-2-(2-fluorophenyl)-7,8,9,10-tetrahydro-imidazo[1,2-c]-quinazoline (Compound 35), m.p. 180°–185° C.
(e) 5-Anilino-2-(2-fluorophenyl)-7,8,9,10-tetrahydro-imidazo[1,2-c]-quinazoline (Compound 36), m.p. 199°–200° C.

EXAMPLE XXI

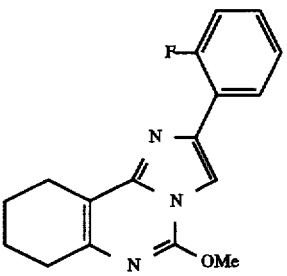

Compound 37

To 10 mL anhydrous methanol was added 100 mg of sodium, and the mixture was stirred to ensure all the sodium had dissolved. Next, 5-Chloro-2-(2-fluorophenyl)-7,8,9,10-tetrahydro-imidazo[1,2-c]-quinazoline (200 mg) was added and the mixture refluxed for 1 h. To this mixture was added 2 mL of acetic acid and the solvent was then removed under reduced pressure. The resulting solid was recrystallized from ethanol and collected to yield 5-Methoxy-2-(2-fluorophenyl)-7,8,9,10-tetrahydro-imidazo[1,2-c]-quinazoline (Compound 37), m.p. 160°–161° C.

EXAMPLE XXII

The following compounds were prepared essentially according to the procedure of Example XXI:
(a) 5-Methoxy-2-phenyl-7,8,9,10-tetrahydro-imidazo[1,2-c]-quinazoline (Compound 38), m.p. 147°–148° C.
(b) 5-Ethoxy-2-(2-fluorophenyl)-7,8,9,10-tetrahydro-imidazo[1,2-c]-quinazoline (Compound 39), m.p. 186°–188° C.
(c) 5-Methoxy-2-phenyl-8,9-dihydro-7H-cyclopent[g]-imidazo[1,2-c]-pyrimidine (Compound 40), m.p. 154°–156° C.

EXAMPLE XXIII

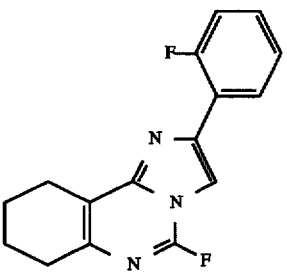

Compound 41

To a solution of 700 mg of potassium fluoride and 200 mg 18-crown-6 in 10 mL of DMF was added 5-Chloro-2-(2-fluorophenyl)-7,8,9,10-tetrahydro-imidazo[1,2-c]-quinazoline (200 mg). This mixture was refluxed for 1.5 h, cooled to room temperature and poured into water. The aqueous solution was extracted with ethyl acetate, the organic layer was separated and dried, and the solvent removed in vacuo to yield 5-Fluoro-2-(2-fluorophenyl)-7,8,9,10-tetrahydro-imidazo[1,2-c]-quinazoline (Compound 41), m.p. 154°–155° C.

EXAMPLE XXIV

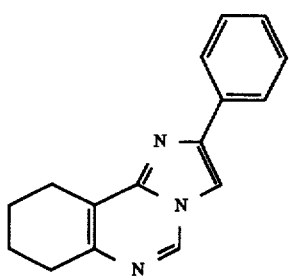

Compound 42

A mixture of 5-Chloro-2-phenyl-7,8,9,10-tetrahydro-imidazo[1,2-c]-quinazoline (200 mg), triethylamine (0.5 mL), and 100 mg of 10% palladium on carbon catalyst in 200 mL ethanol was hydrogenated at 30 psi for 4 hours. The reaction mixture was then filtered through celite, and the solvent was removed in vacuo. The resulting mixture was chromatographed using 30% ethyl acetate/hexane as eluant to yield 2-Phenyl-7,8,9,10-tetrahydro-imidazo[1,2-c]-quinazoline (Compound 42), m.p. 175°–181° C.

EXAMPLE XXV

The following compound was prepared essentially according to the procedure of Example XXIV:

(a) 2-(2'-fluorophenyl)-7,8,9,10-tetrahydro-imidazo[1,2-c]-quinazoline (Compound 43), m.p. 173°–175° C.

EXAMPLE XXVI

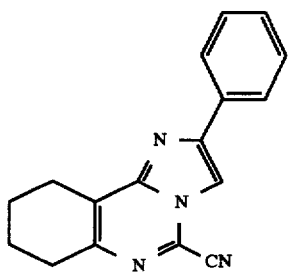

To a solution of 200 mg of potassium cyanide and 300 mg of 18-crown-6 in 20 mL of acetonitrile was added 5-Chloro-2-phenyl-7,8,9,10-tetrahydro-imidazo[1,2-c]-quinazoline (220 mg). The mixture was refluxed for 2 hours, cooled and poured into water. The aqueous layer was extracted with dichloromethane, the organic layer separated and dried and the solvent removed in vacuo. The resultant crude reaction mixture was chromatographed using 15% ethyl acetate/hexane as eluent to yield 5-Cyano-2-phenyl-7,8,9,10-tetrahydro-imidazo[1,2-c]-quinazoline (Compound 44), m.p. 203°–205° C.

EXAMPLE XXVII

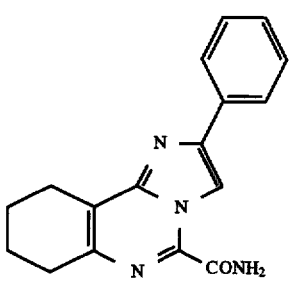

Compound 45

To 5.0 mL of concentrated sulfuric acid was added 5-Cyano-2-phenyl-7,8,9,10-tetrahydro-imidazo[1,2-c]-quinazoline (80 mg). The resulting solution was then heated at 100° C. for 10 min, poured into cold saturated aqueous K₂CO₃ and the solid collected and dried. The solid was extracted with dichloromethane and the solvent removed in vacuo to yield crude product. The product was chromatographed using 5% methanol/methylene chloride as eluent to yield 5-Carboxamido-2-phenyl-7,8,9,10-tetrahydro-imidazo [1,2-c]-quinazoline (Compound 45), m.p. 260°–261° C.

EXAMPLE XXVIII

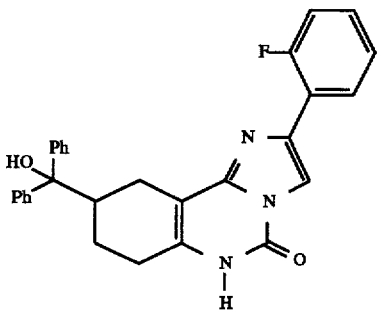

Compound 46

To a solution of 9-Carboethoxy-2-(2-fluorophenyl)-7,8,9,10-tetrahydro-imidazo[1,2-c]-quinazolin-5(6H)-one (110 mg) in 15 mL of anhydrous tetrahydrofuran was added 2 mL of 1.8M phenyllithium. The reaction was allowed to stand for 15 minutes and then quenched with 1 mL of 10% acetic acid. The solvent was removed in vacuo and the crude reaction mixture triterated with water. The solid was then collected and dried to yield 9-(Diphenylhydroxymethyl)-2-(2-fluorophenyl)-7,8,9,10-tetrahydro-imidazo[1,2-c]-quinazolin-5(6H)-one (Compound 46), m.p. 315°–318° C.

EXAMPLE XXIX

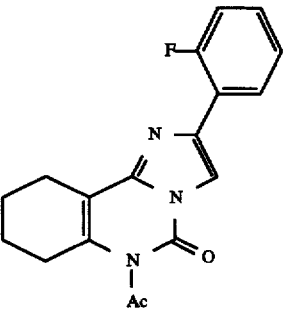

Compound 47

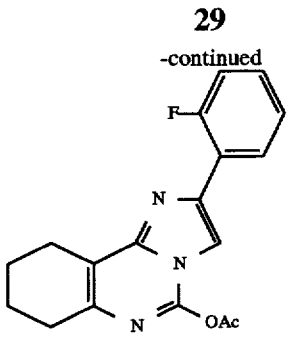

Compound 48

A mixture of 2-(2-Fluorophenyl)-7,8,9,10-tetrahydro-imidazo[1,2-c]-quinazolin-5(6H)-one (283 mg) and 50% sodium hydride (144 mg) in DMF (5 mL) was stirred at room temperature for 15 min. Acetyl chloride (1 mL) was added and stirring was continued for 30 min. The reaction was diluted with ethyl acetate and washed with water. After drying over magnesium sulfate, the solvent was removed in vacuo and the residue was subjected to flash chromatography on silica gel with 30% ethyl acetate in hexane as the eluent to afford 6-Acetyl-2-(2-fluorophenyl)-7,8,9,10-tetrahydro-imidazo[1,2-c]-quinazolin-5(6H)-one (Compound 47) and 5-Acetoxy-2-(2-fluorophenyl)-7,8,9,10-tetrahydro-imidazo[1,2-c]-quinazoline (Compound 48) as white solids.

EXAMPLE XXX

The following additional examples were prepared essentially according to the procedures described in Examples I–VII:

(a) 2-(2,4-Difluorophenyl)-7,8,9,10-tetrahydro-imidazo[1,2-c]-quinazolin-5(6H)-one (Compound 49), m.p.>330° C.

(b) 2-(4-Methoxyphenyl)-7,8,9,10-tetrahydro-imidazo[1,2-c]-quinazolin-5(6H)-one (Compound 50), m.p. 285°–288° C.

(c) 2-(2-Fluoro-4-methoxyphenyl)-7,8,9,10-tetrahydro-imidazo[1,2-c]-quinazolin-5(6H)-one (Compound 51), m.p. 269°–271° C.

(d) 2-(2-Thienyl)-7,8,9,10-tetrahydro-imidazo[1,2-c]-quinazolin-5(6H)-one (Compound 52), m.p.>310° C.

(e) 2-(3-Methylphenyl)-7,8,9,10-tetrahydro-imidazo[1,2-c]-quinazolin-5(6H)-one (Compound 53), m.p.>297°–299° C.

(f) 2-(2,6-Difluorophenyl)-7,8,9,10-tetrahydro-imidazo[1,2-c]-quinazolin-5(6H)-one (Compound 54).

(g) 2-(2,5-Difluorophenyl)-7,8,9,10-tetrahydro-imidazo[1,2-c]-quinazolin-5(6H)-one (Compound 55).

(h) 2-(3-Thienyl)-7,8,9,10-tetrahydro-imidazo[1,2-c]-quinazolin-5(6H)-one (Compound 56).

(i) 2-(4-Ethoxyphenyl)-7,8,9,10-tetrahydro-imidazo[1,2-c]-quinazolin-5(6H)-one (Compound 57), m.p. 278°–281° C.

(j) 2-(4-Methylphenyl)-7,8,9,10-tetrahydro-imidazo[1,2-c]-quinazolin-5(6H)-one (Compound 58).

(k) 2-(2-Fluoro-4-methoxyphenyl)-7,8,9,10-tetrahydro-imidazo[1,2-c]-quinazolin-5(6H)-one (Compound 59), m.p. 224°–226° C.

(l) 2-(2-Thiazolyl)-7,8,9,10-tetrahydro-imidazo[1,2-c]-quinazolin-5(6H)-one (Compound 60), m.p. 321°–323° C.

(m) 2-(4-Methoxyphenyl)-8,9-dihydro-7H-cyclopent[g]-imidazo[1,2-c]-pyrimidin-5(6H)-one (Compound 61). m.p. 256°–259° C.

(n) 2-(4-Methoxyphenyl)-8,9,10,11-tetrahydro-7H-cyclohept[g]-imidazo[1,2-c]pyrimidin-5(6H)-one (Compound 62) m.p. 288°–290° C.

(o) 2-(2-Fluoro-4-methoxyphenyl)-8,9-dihydro-7H-cyclopent[g]-imidazo[1,2-c]-pyrimidin-5(6H)-one (Compound 63). m.p. 265°–270° C.

(p) 2-(2-Fluoro-4-methoxyphenyl)-8,9,10,11-tetrahydro-7H-cyclohept[g]-imidazo[1,2-c]pyrimidin-5(6H)-one (Compound 64) m.p. 282°–284° C.

(q) 2-(5-Methyl-2-oxazolyl)-7,8,9,10-tetrahydro-imidazo[1,2-c]-quinazolin-5(6H)-one (Compound 65), m.p. 291°–293° C.

(r) 2-(5-Methyl-2-(1,3,4-oxadiazolyl)-7,8,9,10-tetrahydro-imidazo[1,2-c]-quinazolin-5(6H)-one (Compound 66), m.p. 346°–348° C.

(s) 2-(4-Ethylphenyl)-7,8,9,10-tetrahydro-imidazo[1,2-c]-quinazolin-5(6H)-one (Compound 67), m.p. 285°–287° C.

(t) 2-(3-Methoxyphenyl)-7,8,9,10-tetrahydro-imidazo[1,2-c]-quinazolin-5(6H)-one (Compound 68), m.p. 307°–310° C.

(u) 2-(3-Ethylphenyl)-7,8,9,10-tetrahydro-imidazo[1,2-c]-quinazolin-5(6H)-one (Compound 69), m.p. 265°–267° C.

EXAMPLE XXXI

The following additional example was prepared essentially according to the procedure described in Example XXIX:

(a) 5-Pivaloyloxy-2-(4-Methoxyphenyl)-7,8,9,10-tetrahydro-imidazo[1,2-c]-quinazoline (Compound 70), m.p. 164°–165° C.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

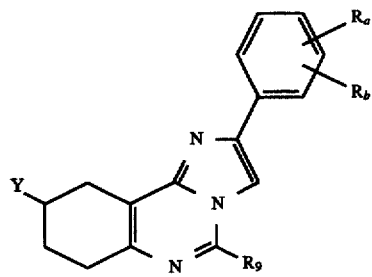

or pharmaceutically acceptable non-toxic salts thereof wherein:

$R_a$ and $R_b$ independently represent halogen, hydroxy, amino, mono or dialkylamino where each alkyl is straight or branched chain alkyl having 1–6 carbon atoms, straight or branched chain lower alkyl having 1–6 carbon atoms, or straight or branched chain lower alkoxy having 1–6 carbon atoms where $R_a$ and $R_b$ each appear at most only once on the phenyl ring;

$R_9$ is hydrogen, halogen, cyano, or alkoxy having 1–6 carbon atoms, amino, phenylamino, mono- or dialkylamino where each alkyl portion is straight or branched chain alkyl having 1–6 carbon atoms, phenylalkyl amino where the alkyl portion is a straight or branched chain lower alkyl having 1–6 carbon atoms; and Y is
- —$OR_4$, —$COR_4$, —$CO_2R_4$, —$OCOR_4$, or $R_4$, where $R_4$ is hydrogen, phenyl, thienyl, straight or branched chain lower alkyl having 1–6 carbon atoms, or phenylalkyl or thienylalkyl where each alkyl portion is straight or branched chain lower alkyl having 1–6 carbon atoms;
- —$CONR_4R_5$ or —$(CH_2)_nNR_4R_5$ where n=0, 1, or 2, $R_4$ is hydrogen, phenyl, thienyl, straight or branched chain lower alkyl having 1–6 carbon atoms, or phenylalkyl or thienylalkyl where each alkyl portion is straight or branched chain lower alkyl having 1–6 carbon atoms, and $R_5$ is hydrogen or straight or branched chain lower alkyl having 1–6 carbon atoms;
- $CONR_4R_5$ or —$(CH_2)_nNR_4R_5$ where n=0, 1, or 2, and $NR_4R_5$ is N-alkyl-piperazyl, -morpholyl, -piperidyl, or -pyrrolidyl where each alkyl portion is straight or branched chain lower alkyl having 1–6 carbon atoms;
- $NR_4CO_2R_6$ where $R_4$ is hydrogen, phenyl, thienyl, straight or branched chain lower alkyl having 1–6 carbon atoms, or phenylalkyl or thienylalkyl where each alkyl portion is straight or branched chain lower alkyl having 1–6 carbon atoms, and $R_6$ is phenyl or straight or branched chain lower alkyl having 1 to 6 carbon atoms; or
- —$C(OH)R_7R_8$ where $R_7$ and $R_8$ are the same or different and represent straight or branched chain lower alkyl having 1 to 6 carbon atoms, phenyl or phenylalkyl where each alkyl portion is straight or branched chain lower alkyl having 1–6 carbon atoms.

* * * * *